US012691438B2

(12) United States Patent
Nishiki et al.

(10) Patent No.: US 12,691,438 B2
(45) Date of Patent: Jul. 28, 2026

(54) CATALYST

(71) Applicant: Mitsubishi Chemical Corporation, Tokyo (JP)

(72) Inventors: Kensuke Nishiki, Tokyo (JP); Takuro Watanabe, Tokyo (JP); Tetsufumi Yamaguchi, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 911 days.

(21) Appl. No.: 17/885,273

(22) Filed: Aug. 10, 2022

(65) Prior Publication Data

US 2022/0387976 A1     Dec. 8, 2022

Related U.S. Application Data

(63) Continuation of application No. PCT/JP2021/007081, filed on Feb. 25, 2021.

(30) Foreign Application Priority Data

Feb. 26, 2020     (JP) ................................. 2020-030809

(51) Int. Cl.

| | |
|---|---|
| *B01J 37/04* | (2006.01) |
| *B01J 23/888* | (2006.01) |
| *B01J 35/60* | (2024.01) |
| *B01J 37/08* | (2006.01) |
| *C07C 45/35* | (2006.01) |
| *C07C 51/25* | (2006.01) |

(52) U.S. Cl.
CPC ........... *B01J 23/8885* (2013.01); *B01J 35/60* (2024.01); *B01J 37/04* (2013.01); *B01J 37/088* (2013.01); *C07C 45/35* (2013.01); *C07C 51/252* (2013.01)

(58) Field of Classification Search
CPC ........ B01J 23/8885; B01J 35/60; B01J 37/04; B01J 37/088; C07C 45/35; C07C 51/252
See application file for complete search history.

(56) References Cited

U.S. PATENT DOCUMENTS

| | | | | |
|---|---|---|---|---|
| 3,928,240 A | * | 12/1975 | Milberger et al. ....... | B01J 23/16 252/467 |
| 2018/0117565 A1 | | 5/2018 | Tamura et al. | |
| 2019/0262800 A1 | | 8/2019 | Nagata et al. | |

FOREIGN PATENT DOCUMENTS

| | | |
|---|---|---|
| CN | 110062656 A | 7/2019 |
| CN | 110152647 A | 8/2019 |
| CN | 110809494 A | 2/2020 |
| EP | 0475351 A1 | 3/1992 |
| EP | 0799642 A1 * | 8/1997 ............. B01J 37/08 |
| JP | H11-033404 A | 2/1999 |
| JP | 2002-253970 A | 9/2002 |
| JP | 2008-284416 A | 11/2008 |
| JP | 2010-201365 A | 9/2010 |
| JP | 2011-115681 A | 6/2011 |
| JP | 2013-188669 A | 9/2013 |
| KR | 10-1992-0003103 B1 | 4/1992 |
| WO | 2016/152964 A1 | 9/2016 |
| WO | 2018/030384 A1 | 2/2018 |

OTHER PUBLICATIONS

JP2008284416A (Ooyanai et al.; IDS reference; English language machine translation) (Year: 2008).*
J. Catal. 2009, 262, 35-43 (Ivars et al.) (Year: 2009).*
International Search Report issued in related International Patent Application No. PCT/JP2021/007081 dated Apr. 27, 2021.
Office Action issued in Indonesian Patent Application No. P00202208961 dated Sep. 6, 2023.
Office Action issued in corresponding Chinese Patent Application No. 202180014630.2 dated Jan. 23, 2024.
Chemical Bulletin, the 11th, Shǐjen et al., "New unsaturated aldehydes," pp. 38 to 40, Dec. 30, 1996 (Dec. 30, 1996) (see the Chinese Office Action).
Compiled by Chemical Dictionary Compilation Committee, "Chemical Dictionary 8", Paper Edition No. 23, Kyoritsu Publishing Company, Nov. 10, 1979, p. 179 (see partial English translation).
Office Action issued in Japanese Patent Application No. 2022-503686 dated Jun. 27, 2023.
Office Action issued in corresponding Indian Patent Application No. 202247046753 dated Oct. 12, 2022.
Office Action issued in corresponding Korean Patent Application No. 10-2022-7026392, dated Jun. 26, 2024.
Office Action issued in corresponding Saudi Arabian Patent Application No. 522440293, dated Jul. 18, 2024.
Hearing Notice issued in related Indian Patent Application No. 202247046753 dated Apr. 19, 2023.
Office Action issued in corresponding Singaporean Patent Application No. 11202252057E, dated Jun. 5, 2025.

* cited by examiner

*Primary Examiner* — Amy C Bonaparte
*Assistant Examiner* — Derek Rhoades
(74) *Attorney, Agent, or Firm* — Morgan, Lewis & Bockius LLP

(57) ABSTRACT

An object of the present invention is to provide a catalyst capable of improving the selectivity of unsaturated aldehydes and unsaturated carboxylic acids, and a catalyst containing molybdenum, antimony, bismuth, and iron, wherein an atom ratio of the antimony to the molybdenum on a surface of the catalyst is greater than an atom ratio of the antimony to the molybdenum in the entire catalyst is provided.

15 Claims, No Drawings

CATALYST

CROSS-REFERENCE TO RELATED APPLICATIONS

This application is a continuation filing of, and claims priority under 35 U.S.C. § 111(a) to, International Application No. PCT/JP2021/007081, filed on Feb. 25, 2021, and therethrough claims priority under 35 U.S.C. § 119 to Japanese Patent Application No. 2020-030809 filed in Japan on Feb. 26, 2020, the content of which is incorporated herein by reference.

BACKGROUND OF THE INVENTION

Field of the Invention

The present invention relates to a catalyst. In more detail, the present invention mainly relates to a catalyst that is used at the time of producing unsaturated aldehydes and/or unsaturated carboxylic acids. More specifically, the present invention relates to a catalyst that is suitably used at the time of synthesizing corresponding unsaturated aldehydes and/or unsaturated carboxylic acids by performing a gas phase oxidation of propylene, isobutylene, tertiary butanol (hereinafter, abbreviated as TBA), or methyl tertiary butyl ether (hereinafter, abbreviated as MTBE).

Priority is claimed on Japanese Patent Application No. 2020-030809, filed Feb. 26, 2020, the content of which is incorporated herein by reference.

Description of the Related Art

Methods for producing an unsaturated aldehyde or an unsaturated carboxylic acid by performing a gas phase oxidation reaction in the presence of a metal oxide catalyst using an organic compound such as propylene, isobutylene, t-butyl alcohol, or methyl-t-butyl ether are known. For example, Japanese Patent Application Publication No. 2011-115681 (hereafter, Patent Document 1) describes an example in which a gas phase oxidation reaction is performed using isobutylene in the presence of a metal oxide catalyst containing molybdenum, tungsten, cesium, antimony, bismuth, iron, nickel, cobalt, and lead as metal elements to produce methacrolein and methacrylic acid. In addition, Japanese Patent Application Publication No. 2013-188669 (hereafter, Patent Document 2) describes an example in which a gas phase oxidation reaction is performed in the presence of a metal oxide catalyst containing molybdenum, antimony, bismuth, and iron to produce methacrolein and methacrylic acid.

BRIEF SUMMARY OF THE INVENTION

Technical Problem

However, according to studies by the present inventors and the like, it was clarified that the catalysts described in Patent Document 1 and Patent Document 2 do not always have sufficient performance and generate many by-products in some cases. Since these problems affect the yields of unsaturated aldehydes and unsaturated carboxylic acids, actually, there is a desire for additional improvement in the performance of catalysts.

An object of the present invention is to provide a catalyst capable of improving the selectivity of unsaturated aldehydes and unsaturated carboxylic acids.

Solution to Problem

In the present invention, it was found that, in a catalyst containing at least molybdenum, bismuth, antimony, and iron, when the antimony distribution in the catalyst is adjusted, it is possible to produce unsaturated aldehydes and/or unsaturated carboxylic acids with a high selectivity.

That is, the present invention is as follows.

[1] A catalyst containing molybdenum, antimony, bismuth, and iron,
   wherein an atom ratio of the antimony to the molybdenum on a surface of the catalyst is greater than an atom ratio of the antimony to the molybdenum in an entire catalyst.

[2] The catalyst according to [1], wherein a ratio B/A is 1.0 or more, in which, A is an atom ratio of the antimony to the molybdenum calculated by Inductively Coupled Plasma (ICP) emission spectroscopy, and B is a peak area ratio of the antimony to the molybdenum calculated by X-ray photoelectron spectroscopy.

[3] The catalyst according to [2], wherein the B/A is 10.0 or less.

[4] The catalyst according to [2] or [3], wherein A is 0.04 or more and 0.20 or less.

[5] The catalyst according to any one of [2] to [4], wherein B is 0.05 or more and 0.50 or less.

[6] The catalyst according to any one of [1] to [5], wherein the catalyst is a metal oxide catalyst.

[7] The catalyst according to any one of [1] to [6], wherein the catalyst comprises Formula (1):

$$Mo_aBi_bFe_cSb_dM_eX_fY_gSi_hO_i \qquad (1)$$

wherein, in Formula (1),
   Mo, Bi, Fe, Sb, Si, and O represent molybdenum, bismuth, iron, antimony, silicon, and oxygen, respectively,
   M represents at least one selected from the group consisting of cobalt and nickel,
   X represents at least one selected from the group consisting of zinc, chromium, lead, manganese, calcium, magnesium, niobium, silver, barium, tin, tantalum, tungsten, phosphorus, boron, sulfur, selenium, tellurium, cerium and titanium,
   Y represents at least one element selected from the group consisting of cesium, lithium, sodium, potassium, rubidium, and thallium,
   a, b, c, d, e, f, g, h and i represent an atomic ratio, and, when a=12, b=0.01 to 3.00, c=0.01 to 5.00, d=0.01 to 5.00, e=0.00 to 12.00, f=0.00 to 8.00, g=0.001 to 2.00, h=0.00 to 20.00, and
   i represents an oxygen atom ratio required to satisfy a valence of each component.

[8] A method of producing an unsaturated aldehyde and/or an unsaturated carboxylic acid, comprising:
   performing a gas phase oxidation reaction of a corresponding organic compound as a raw material in presence of the catalyst according to any one of [1] to [7].

[9] A method of producing a catalyst containing molybdenum and antimony, comprising:
   mixing a molybdenum compound, an antimony compound, and a dispersant to produce a mixture; and
   calcinating the mixture to produce the catalyst,
   wherein, in the mixing, the dispersant is added before the antimony compound is dissolved.

[10] The method according to [9], wherein the dispersant comprises a hydrazine compound.

[11] The method according to [9] or [10], wherein the antimony compound has a particle size of 0.21 μm or more and 7.90 μm or less.

Advantageous Effects of Invention

According to the present invention, it is possible to provide a catalyst capable of improving the selectivity of unsaturated aldehydes and unsaturated carboxylic acids.

DETAILED DESCRIPTION OF THE INVENTION

Hereinafter, an embodiment according to the present invention will be described below, but the present invention is not limited to the following.

[Catalyst]

A catalyst according to the present embodiment is a catalyst containing molybdenum, antimony, bismuth, and iron and is preferably a metal oxide catalyst. In addition, an atom ratio of the antimony to the molybdenum on a surface of the catalyst is greater than an atom ratio the antimony to the molybdenum in the entire catalyst. When the atom ratio of the antimony to the molybdenum on the surface of the catalyst is greater than the ratio the antimony to the molybdenum in the entire catalyst, unsaturated aldehydes such as methacrolein and/or unsaturated carboxylic acids such as methacrylic acid can be produced from a raw material organic compound with a high selectivity. The reason therefor is not clear, but the following reasons are conceivable. It is believed that the antimony plays a role of, for example, an oxidation reaction activity site from isobutylene to methacrolein on the surface of the catalyst, and it is believed that, when the atom ratio of the antimony to the molybdenum is greater than the atom ratio of the antimony to the molybdenum in the entire catalyst, that is, when the amount of the antimony on the catalyst surface is sufficient, a selective oxidation reaction to an unsaturated aldehyde such as methacrolein and/or an unsaturated carboxylic acid such as methacrylic acid proceeds, and the selectivity of the unsaturated aldehyde such as methacrolein and/or the unsaturated carboxylic acid such as methacrylic acid improves.

Furthermore, a ratio B/A is preferably 1.0 or more, in which A is an atom ratio of the antimony to the molybdenum calculated by Inductively Coupled Plasma (ICP) emission spectroscopy, and B is a peak area ratio of the antimony to the molybdenum calculated by X-ray photoelectron spectroscopy. When B/A satisfies the above-described range, unsaturated aldehydes such as methacrolein and/or unsaturated carboxylic acids such as methacrylic acid can be produced from a raw material organic compound with a high selectivity. The reason therefor is not clear, but the following reasons are conceivable. It is believed that the antimony plays a role of, for example, an oxidation reaction activity site from isobutylene to methacrolein on the surface of the catalyst, and when B/A is 1.0 or more, that is, the amount of the antimony on the surface of the catalyst is sufficient, a selective oxidation reaction to an unsaturated aldehyde such as methacrolein and/or an unsaturated carboxylic acid such as methacrylic acid proceeds, and it is possible for the selectivity of the unsaturated aldehyde such as methacrolein and/or the unsaturated carboxylic acid such as methacrylic acid to improve, which is preferable.

In particular, the B/A value is more preferably 1.2 or more, still more preferably 1.5 or more, still more preferably 1.8 or more, particularly preferably 2.0 or more, and most preferably 2.3 or more. On the other hand, in particular, the B/A value is preferably 10.0 or less, more preferably 8.0 or less, still more preferably 6.0 or less, far still more preferably 4.0 or less, particularly preferably 3.5 or less, and most preferably 3.0 or less.

The A value is not particularly limited as long as the B/A is satisfied, but is preferably 0.04 or more, more preferably 0.06 or more, and particularly preferably 0.08 or more and, on the other hand, preferably 0.20 or less, more preferably 0.16 or less, and particularly preferably 0.12 or less in order to improve the selectivity of unsaturated aldehydes such as methacrolein and/or unsaturated carboxylic acids such as methacrylic acid.

The B value is not particularly limited as long as the B/A is satisfied, but is preferably 0.05 or more, more preferably 0.13 or more, still more preferably 0.15 or more, and particularly preferably 0.17 or more and, on the other hand, preferably 0.50 or less, more preferably 0.40 or less, still more preferably 0.35 or less, and particularly preferably 0.30 or less in order to improve the selectivity of unsaturated aldehydes such as methacrolein and/or unsaturated carboxylic acids such as methacrylic acid.

The atom ratio of the antimony that configure the catalyst is not particularly limited; however, in order to improve the selectivity of unsaturated aldehydes and/or unsaturated carboxylic acids, a ratio (d) of the number of the antimony atoms to the number of molybdenum atoms of 12 is preferably 0.01 or more, more preferably 0.03 or more, and particularly preferably 0.05 or more and, on the other hand, preferably 5.00 or less, more preferably 3.00 or less, and particularly preferably 2.00 or less.

The atom ratio of bismuth that configure the catalyst is not particularly limited; however, in order to improve the selectivity of unsaturated aldehydes and/or unsaturated carboxylic acids, a ratio (b) of the number of the bismuth atoms to the number of the molybdenum atoms of 12 is preferably 0.01 or more, more preferably 0.03 or more, and particularly preferably 0.05 or more and, on the other hand, preferably 3.00 or less, more preferably 2.00 or less, and particularly preferably 1.00 or less.

The atom ratio of iron that configure the catalyst is not particularly limited; however, in order to improve the selectivity of unsaturated aldehydes and/or unsaturated carboxylic acids, a ratio (c) of the number of the iron atoms to the number of the molybdenum atoms of 12 is preferably 0.01 or more, more preferably 0.10 or more, still more preferably 1.00 or more, and particularly preferably 1.50 or more and, on the other hand, preferably 5.00 or less, more preferably 4.00 or less, and particularly preferably 3.00 or less.

As described above, the catalyst contains antimony, molybdenum, bismuth, and iron, but may contain different elements other than these elements. As such elements, for example, cobalt, nickel, zinc, chromium, lead, manganese, calcium, magnesium, niobium, silver, barium, tin, tantalum, tungsten, phosphorus, boron, sulfur, selenium, tellurium, cerium, titanium, cesium, lithium, sodium, potassium, rubidium, or thallium are exemplary examples.

Among the different elements, the catalyst preferably contains at least one element selected from the group consisting of cobalt and nickel and more preferably further contains at least one element selected from the group consisting of cesium, lithium, sodium, potassium, rubidium, and thallium.

The atom ratio of cobalt and nickel that configure the catalyst is not particularly limited; however, in order to improve the selectivity of unsaturated aldehydes and/or unsaturated carboxylic acids, a ratio (e) of the total atom number of the cobalt atoms and the nickel atoms to the number of the molybdenum atoms of 12 is 0.00 or more, preferably 0.01 or more, more preferably 0.10 or more, still more preferably 1.00 or more, and particularly preferably 3.00 or more and, on the other hand, preferably 12.00 or less, more preferably 10.00 or less, and particularly preferably 9.00 or less.

The ratio of the total atom number of zinc atoms, chromium atoms, lead atoms, manganese atoms, calcium atoms, magnesium atoms, niobium atoms, silver atoms, barium atoms, tin atoms, tantalum atoms, tungsten atoms, phosphorus atoms, boron atoms, sulfur atoms, selenium atoms, tellurium atoms, cerium atoms, and titanium atoms that configure the catalyst is not particularly limited; however, in order to improve the selectivity of unsaturated aldehydes and/or unsaturated carboxylic acids, a ratio (f) of the total atom number of these atoms to the number of the molybdenum atoms of 12 is 0.00 or more, more preferably 0.10 or more, still more preferably 0.20 or more, and particularly preferably 0.50 or more and, on the other hand, preferably 8.00 or less, more preferably 6.00 or less, and particularly preferably 4.00 or less.

The ratio of the total atom number of cesium atoms, lithium atoms, sodium atoms, potassium atoms, rubidium atoms, and thallium atoms that configure the catalyst is not particularly limited; however, in order to improve the selectivity of unsaturated aldehydes and/or unsaturated carboxylic acids, a ratio (g) of the total atom number of these atoms to the number of the molybdenum atoms of 12 is 0.001 or more, more preferably 0.05 or more, still more preferably 0.10 or more, and particularly preferably 0.20 or more and, on the other hand, preferably 1.80 or less, more preferably 1.60 or less, and particularly preferably 1.40 or less.

In addition, the catalyst may or may not have a carrier for supporting the above-described elements. The carrier is not particularly limited, and silica, alumina, silica-alumina, magnesia, titania, silicon carbide, and the like are exemplary examples. Among these, when the carrier is used, silica is preferable as the carrier in order to prevent the reaction of the carrier itself. When the carrier is used in the catalyst in the present invention, the carrier is also regarded as a component of the catalyst.

When the catalyst has a silica carrier, the ratio of silicon atoms that configures the catalyst is not particularly limited; however, in order to improve the selectivity of unsaturated aldehydes and/or unsaturated carboxylic acids, a ratio (h) of the silicon atoms to the number of the molybdenum atoms of 12 is 0.00 or more and, on the other hand, preferably 20.00 or less, more preferably 15.00 or less, and particularly preferably 10.00 or less.

In particular, the catalyst is preferably a catalyst comprising Formula (1).

$$Mo_aBi_bFe_cSb_dM_eX_fY_gSi_hO_i \qquad (1)$$

In Formula (1):
Mo, Bi, Fe, Sb, Si, and O represent molybdenum, bismuth, iron, antimony, silicon, and oxygen, respectively.
M represents at least one selected from the group consisting of cobalt and nickel.
X represents at least one selected from the group consisting of zinc, chromium, lead, manganese, calcium, magnesium, niobium, silver, barium, tin, tantalum, tungsten, phosphorus, boron, sulfur, selenium, tellurium, cerium, and titanium.
Y represents at least one selected from the group consisting of cesium, lithium, sodium, potassium, rubidium, and thallium.

a, b, c, d, e, f, g, h, and i represent an atomic ratio, and, when a is =12, b=0.01 to 3.00, c=0.01 to 5.00, d=0.01 to 5.00, e=0.00 to 12.00, f=0.00 to 8.00, g=0.001 to 2.00, and h=0.00 to 20.00.
i represents an oxygen atom ratio required to satisfy a valence of each components.

The (b) to (h) values in Formula (1) have the same meanings as (b) to (h) described for each of the above-described elements, and preferable ranges thereof are also the same as the (b) to (h) values described for each the above-described elements.

The composition of the catalyst can be confirmed by carrying out elemental analysis by Inductively Coupled Plasma (ICP) spectrometry, a fluorescent X-ray analysis method, atomic absorption spectrometry, or the like.

For the composition of the entire catalyst, Inductively Coupled Plasma (ICP) emission spectroscopy is preferable. ICP emission spectroscopy is a method of measuring spectral lines that are emitted when an atom contained in a sample is excited by the energy of plasma applied from the outside and the excited atoms return to a low energy level. The entire composition of the sample can be calculated by carrying out ICP emission spectroscopic analysis on a solution in which the sample has been dissolved.

For the surface composition of the catalyst, X-ray photoelectron spectroscopy (XPS) is preferable. The X-ray photoelectron spectroscopy is a method by which the composition and chemical state of elements that configure a sample surface by irradiating the sample surface with X-rays and measuring the kinetic energy of a photoelectron that is emitted from the sample surface and can also be used for catalysts. Ordinarily, it is possible to obtain information on elements present in a range of several nanometers from the sample surface, to obtain information on the composition and chemical state of the surface of the catalyst, and to calculate the composition of the surface the catalyst.

The catalyst shape is not particularly limited, and a spherical shape, a cylindrical shape, a ring shape, a star shape, any shapes such as a granule shape formed when the catalyst is molded, then, crushed, and classified, and the like are exemplary examples.

The catalyst density is not particularly limited, but is preferably 0.2 g/cm³ or more, more preferably 0.5 g/cm³ or more, and still more preferably 1.0 g/cm³ or more in order to improve the durability of the catalyst and is preferably 50.0 g/cm³ or less, more preferably 30.0 g/cm³ or less, and still more preferably 20.0 g/cm³ or less in order to improve the selectivity of unsaturated aldehydes and/or unsaturated carboxylic acids.

The catalyst mass is not particularly limited, but is preferably 0.002 g/catalyst or more, more preferably 0.005 g/catalyst or more, and particularly preferably 0.010 g/piece or more in order to stably produce unsaturated aldehydes and/or unsaturated carboxylic acids over a long period of time and, on the other hand, is preferably 0.50 g/catalyst or less, more preferably 0.30 g/catalyst or less, and particularly preferably 0.20 g/catalyst or less in order to improve the selectivity of unsaturated aldehydes and/or unsaturated carboxylic acids.

The outer diameter of the catalyst is not particularly limited, but the outer diameter is preferably 0.01 cm or more, more preferably 0.05 cm or more, and particularly preferably 0.10 cm or more in order to stably produce unsaturated aldehydes and/or unsaturated carboxylic acids over a long period of time and is preferably 2.00 cm or less, more preferably 1.50 cm or less, and particularly preferably 1.00 cm or less in order to improve the catalyst strength.

The catalyst volume is not particularly limited, but is preferably 0.0002 cm³ or more, more preferably 0.0003 cm³ or more, and particularly preferably 0.0005 cm³ or more in order to stably produce unsaturated aldehydes and/or unsaturated carboxylic acids over a long period of time and, on the other hand, is preferably 5.00 cm³ or less, more preferably 1.00 cm³ or less, and particularly preferably 0.50 cm³ or less in order to improve the selectivity of unsaturated aldehydes and/or unsaturated carboxylic acids.

The outer surface area of the catalyst is not particularly limited, but is preferably 0.01 cm² or more, more preferably 0.02 cm² or more, and particularly preferably 0.05 cm² or more in order to stably produce unsaturated aldehydes and/or unsaturated carboxylic acids over a long period of time and, on the other hand, is preferably 4.00 cm² or less, more preferably 3.00 cm² or less, and particularly preferably 2.00 cm² or less in order to improve the selectivity of unsaturated aldehydes and/or unsaturated carboxylic acids.

The packed bulk density of the catalyst is not particularly limited, but is preferably 0.20 g/cm³ or more, more preferably 0.30 g/cm³ or more, and still more preferably 0.40 g/cm³ or more in order to stably produce unsaturated aldehydes and/or unsaturated carboxylic acids over a long period of time and, on the other hand, is preferably 1.00 g/cm³ or less, more preferably 0.90 g/cm³ or less, and still more preferably 0.80 g/cm³ or less in order to improve the selectivity of unsaturated aldehydes and/or unsaturated carboxylic acids. The packed bulk density of the catalyst means a value calculated from the total mass of the catalyst when a 100 ml graduated cylinder is packed with the catalyst by a method according to JIS-K 7365.

[Method for Producing Catalyst]

A method of producing a catalyst according to the present embodiment is not particularly limited as long as the catalyst contains molybdenum, antimony, bismuth, and iron, and the atom ratio of the antimony to the molybdenum on the surface the catalyst is greater than the atom ratio of the antimony to the molybdenum in the entire catalyst, and a raw material of each element that configures the catalyst (hereinafter, abbreviated as the catalyst raw material in some cases) needs to be adjusted such that each element is contained at a predetermined ratio so as to obtain a desired catalyst composition. The ratio of the number of the antimony atoms to the number of the molybdenum atoms of a catalyst to be obtained can be adjusted by adjusting the amount of an antimony raw material that is used as the catalyst raw material, the average particle size of the antimony raw material, and the amount of a dispersant used as a catalyst production raw material. In particular, when a hydrazine compound is used as the dispersant, there is a tendency that the atom ratio of the antimony to the molybdenum on the surface of the catalyst becomes greater than the atom ratio of the antimony to the molybdenum in the entire catalyst. Therefore, the atom ratio of the antimony to the molybdenum is preferably adjusted by using a predetermined amount of the hydrazine compound and then adjusting the average particle size and amount of the antimony raw material used. Specifically, a catalyst can be produced by mixing a predetermined amount of the antimony raw material having a specific average particle size, a solvent, and a predetermined amount of the hydrazine compound to prepare a raw material liquid (hereinafter, referred to as the raw material liquid preparation step in some cases) and then molding the catalyst using the raw material liquid (hereinafter, referred to as the molding step in some cases).

<Raw Material Liquid Preparation Step>

The catalyst raw material is not particularly limited; however, usually, an oxide, chloride, hydroxide, sulfate, nitrate, carbonate, ammonium salt, and acetate of each element, a mixture thereof, and the like can be used.

A molybdenum raw material is not particularly limited, examples thereof include ammonium paramolybdate, molybdenum trioxide, molybdenum chloride, and the like, and ammonium paramolybdate is particularly preferable.

The antimony raw material is not particularly limited, and antimony trichloride, antimony acetate, antimony trioxide, and the like are exemplary examples. Among these, antimony trioxide is preferably used. As described above, the B/A value of a catalyst to be obtained is preferably adjusted by using a predetermined amount of the dispersant and then adjusting the amount of the antimony raw material used and/or the average particle size of the antimony raw material. In preparation of the raw material liquid, the B/A value of the catalyst tends to increase when an antimony raw material having a large average particle size, up to a certain average particle size, is used, and, on the other hand, the B/A value of the catalyst tends to decrease when an antimony raw material having a small average particle size is used. Therefore, the average particle size of the antimony raw material to be used needs to be appropriately selected in consideration of the amount of the dispersant, which will be described below, used such that a desired B/A value can be obtained. Although the balance with the amount of the antimony raw material used and the amount of the dispersant needs to be taken into account, an antimony raw material having an average particle size of 0.21 μm or more and 7.90 μm or less is preferably selected. The reason therefor is that, when the average particle size of the antimony raw material is 0.21 μm or more, in the catalyst preparation step, since only a certain amount of antimony is dissolved, the remaining antimony forms a composite oxide on the surface of the catalyst, and thus the atom ratio of the antimony to the molybdenum on the surface of the catalyst becomes greater than the atom ratio of the antimony to the molybdenum in the entire catalyst, and it is possible for the selectivity of unsaturated aldehydes such as methacrolein and/or unsaturated carboxylic acids such as methacrylic acid to improve, which is preferable. In this case, the antimony raw material is preferably antimony trioxide. In addition, the amount of the antimony raw material used is not particularly limited and may be selected so as to obtain a desired catalyst composition, but the B/A value of a catalyst to be obtained tends to increase as the amount of the antimony raw material used increases.

In particular, the average particle size is preferably 0.40 μm or more, more preferably 0.60 μm or more, and particularly preferably 0.80 μm or more in order to improve the selectivity of unsaturated aldehydes such as methacrolein and/or unsaturated carboxylic acids such as methacrylic acid, and, on the other hand, is preferably 6.00 μm or less, more preferably 4.00 μm or less, and particularly preferably 2.00 μm or less in order to improve the selectivity of unsaturated aldehydes and/or unsaturated carboxylic acids.

The bismuth raw material is not particularly limited, and bismuth nitrate, bismuth oxide, bismuth subcarbonate, and the like are exemplary examples.

As an iron raw material, various raw materials such as iron nitrate, iron hydroxide, and iron trioxide can be used, and ferric nitrate is particularly preferable.

In addition, when the catalyst contains different elements other than molybdenum, antimony, and bismuth, various raw materials such as oxides, carbonates, chlorides, ammonium salts, nitrates, acetates, sulfates, and the like of each element can be used.

In the catalyst raw material, one kind of each element may be used singly or two or more kinds of each element may be jointly used.

The dispersant described above is used to improve the solubility of the antimony raw material. No detailed mechanism of the solubility of antimony is known, but the dissolution of antimony is promoted by a reduction reaction of molybdenum, that is, the reduction reaction from $Mo^{VI}$ to $Mo^{V}$. That is, the dispersant is, herein, a reducing agent. As the reducing agent, lithium aluminum hydride ($LiAlH_4$), sodium borohydride ($NaBH_4$), hydrazine, oxalic acid, formic acid, ascorbic acid, and the like are exemplary examples.

In addition, as described above, a hydrazine compound is preferably used as the dispersant in order to adjust the B/A value of the catalyst. The hydrazine compound refers to a compound containing —NHNH— in the structure, and, as such a compound, organic hydrazine compounds such as hydrazine, hydrazine monohydrate, and hydrazine carbonate, methylhydrazine, phenylhydrazine, acetyl hydrazine, and the like are exemplary examples. Among them, as the hydrazine compound, an inorganic hydrazine compound containing no organic groups in the structure is preferable for the following reason. The inorganic hydrazine compound generates an inorganic compound such as nitrogen or water due to a reduction reaction in the raw material liquid. Therefore, since the inorganic hydrazine compound does not remain as an organic compound in the raw material liquid, it is believed that the influence on the formation of a composite oxide structure, a defect such as poor drying in a drying step after preparation, and the influence on other post steps or the like are small.

When the hydrazine compound is used, it becomes easy to obtain a catalyst having a B/A value of 1.0 or more, the B/A value of a catalyst to be obtained increases as the amount of the hydrazine compound used increases, up to a certain amount. On the other hand, when the amount of the hydrazine compound exceeds a certain amount, the B/A value tends to decrease. Therefore, the amount of the hydrazine compound used may be adjusted in consideration of the amount of the antimony raw material used and the average particle size of the antimony raw material, but the proportion of the hydrazine compound raw material in the raw material liquid is preferably set to 0.01 mol or more and 0.49 mol or less with respect to 12 mol of the molybdenum atoms when an antimony raw material having an average particle size of 0.21 μm or more and 7.90 μm or less is used.

In particular, the proportion of the hydrazine compound raw material in the raw material liquid is preferably 0.03 mol or more and more preferably 0.06 mol or more in order to improve the selectivity of unsaturated aldehydes such as methacrolein and/or unsaturated carboxylic acids such as methacrylic acid, and the proportion of the hydrazine compound raw material in the raw material liquid is preferably is particularly preferably 0.09 mol or more with respect to 12 mol of the molybdenum atoms and, on the other hand, is preferably 0.45 mol or less, more preferably 0.40 mol or less, and particularly preferably 0.35 mol or less in order to improve the selectivity of unsaturated aldehydes and/or unsaturated carboxylic acids.

In addition, as described above, the B/A value tends to fluctuate depending on the amount of the antimony raw material used. That is, the B/A value tends to increase as the amount of the antimony raw material used increases, and the B/A value tends to decrease as the amount of the antimony raw material used decreases. However, in order to obtain a catalyst having a desired composition, it is preferable that the amount of antimony necessary for a desired catalyst is adjusted with the antimony raw material and then the B/A value is adjusted with the particle sizes of the antimony raw material to be used and the amount of the hydrazine compound.

The solvent is not particularly limited as long as the solvent is capable of dissolving or dispersing the catalyst raw materials, but at least water is preferably used, 50% by mass or more of the entire solvent is preferably water, and water alone may be used. The solvent may contain an organic solvent in addition to water. The organic solvent is not particularly limited, and alcohols, acetone, and the like are exemplary examples.

The raw material liquid can be prepared by mixing the catalyst raw materials, the hydrazine compound, and the solvent. The raw material liquid may be prepared by adding the catalyst raw materials and the hydrazine compound to the solvent in any order or may be prepared by preparing a plurality of solutions or slurries by dissolving or dispersing one or more kinds of the catalyst raw materials and/or the hydrazine compound in the solvent in advance and mixing these solutions or slurries.

Hereinafter, a preferable production example of the raw material liquid having the composition represented by the formula (1) will be described. The production example includes a first step, a second step, and a third step as described below. Various catalyst raw materials, a hydrazine compound, and a solvent are as described above.

First step: A step of preparing a solution or slurry containing the molybdenum raw material, the bismuth raw material, the antimony raw material, a raw material of an element represented by X in the formula (1), a raw material of an element represented by Y in the formula (1), and the hydrazine compound.

Second step: A step of preparing a solution or slurry containing the iron raw material and a raw material of an element represented by M in the formula (1).

Third step: A step of mixing the solutions or slurries obtained in the first step and the second step to obtain a raw material liquid.

In the first step, the molybdenum raw material, the bismuth raw material, the antimony raw material, a raw material of an element represented by X in the formula (1), a raw material of an element represented by Y, and the hydrazine compound are dissolved or dispersed in a solvent to prepare a solution or a slurry. The amounts of various raw materials used may be appropriately adjusted so as to obtain a desired catalyst composition. The mass of the solvent is not particularly limited, but is preferably set to 70 parts by mass or more and 400 parts by mass or less with respect to a total of 100 parts by mass of the catalyst raw materials.

As described above, the amount of the hydrazine compound added needs to be an amount adjusted such that the B/A value of a catalyst to be obtained becomes a desired value. In addition, the hydrazine compound may be all added at one time or may be divided and added in a plurality of times. The hydrazine compound may be added not only in the first step but also in the second step to be described below, but the hydrazine compound is preferably all added in the first step. The reason therefor is that the hydrazine compound promotes the reduction of molybdenum and consequently makes the amount of antimony that is disposed on the surface of the catalyst tend to increase, which makes it believed preferable for the hydrazine compound to be all added in the first step where the molybdenum raw material is used.

In the second step, a solution or slurry containing the iron raw material and a raw material of an element represented by M in the formula (1) is prepared. The amounts of various raw materials used may be appropriately adjusted so as to obtain a desired catalyst composition. The amount of the solvent that is used is not particularly limited, but is preferably 30 parts by mass or more and 230 parts by mass or less with respect to a total of 100 parts by mass of the catalyst raw materials.

The order of the first step and the second step is not limited, the second step may be carried out after the first step, the first step may be carried out after the second step, and the first step and the second step may be carried out at the same time.

In the third step, a raw material liquid can be obtained by mixing the slurry or solution obtained in the first step and the slurry or solution obtained in the second step.

The obtained raw material liquid may be aged. The raw material liquid is preferably aged at the boiling point of the solvent or lower when being aged. When a solvent having a boiling point of 160° C. or higher is used, the raw material liquid is preferably held in a temperature range of 60° C. or higher and 150° C. or lower when being aged. This makes it possible to further improve the catalyst performance.

<Molding Step>

Next, the obtained raw material liquid is dried, calcinated, and molded, whereby a catalyst can be obtained.

The raw material liquid can be dried using various well-known dryers such as a box-shaped dryer and a spray dryer. The drying conditions are not particularly limited as long as the raw material liquid can be dried, for example, when a box-shaped dryer is used, the temperature is preferably 30° C. or higher and 150° C. or lower, and, when a spray dryer is used, the inlet temperature is preferably 100° C. or higher and 500° C. or lower. Drying of the raw material liquid makes it possible to suppress the adhesion of a dry powder and improve the yield.

Next, the obtained dried product is calcinated. The dried product may be calcinated only once or may be calcinated a plurality of times in combination with a molding step to be described below. For example, primary calcination may be carried out first, the molding step to be described below may be carried out on the obtained primarily-calcinated product, and secondary calcination may be carried out on the obtained molded product or primary calcination and secondary calcination may be carried out and the molding step may be carried out on the obtained catalyst. The dried product is preferably calcinated under the flow of an oxygen-containing gas such as air or under the flow of an inert gas such as nitrogen, carbon dioxide, helium, or argon. The calcination temperature is preferably in a temperature range of 200° C. or higher and 700° C. or lower. The time taken for the dried product to reach a predetermined calcination temperature and be held at the temperature (hereinafter, referred to as the calcination time in some cases) is appropriately selected depending on the target catalyst.

Between the above-described methods, it is preferable to carry out primary calcination, then, molding, and secondary calcination on the dried product. At this time, the calcination temperature of the primary calcination is preferably 200° C. or higher and more preferably 250° C. or higher and, on the other hand, is preferably 600° C. or lower and more preferably 450° C. or lower. The calcination time of the primary calcination is preferably 0.5 hours or longer and 5 hours or shorter. The type of a calcination furnace and the method at the time of the primary calcination are not particularly limited, and, for example, the dried product may be calcinated in a fixed state using a box-type calcination furnace, a tunnel-type calcination furnace, or the like or the dried product may be calcinated using a rotary kiln or the like while being caused to flow.

The calcination temperature of the secondary calcination is preferably 300° C. or higher and more preferably 400° C. or higher and, on the other hand, is preferably 700° C. or lower and more preferably 600° C. or lower. The calcination time of the secondary calcination is not particularly limited, but is preferably 10 minutes or longer and more preferably 1 hour or longer and is preferably 10 hours or shorter since a higher performance catalyst can be obtained. The type of a calcination furnace and the method at the time of the secondary calcination are not particularly limited, and, for example, the molded product or the primarily-calcinated product may be calcinated in a fixed state using calcination furnace, for example, a box-type calcination furnace, a tunnel-type calcination furnace, or the like. In addition, the molded product or the primarily-calcinated product may be calcinated using a rotary calcination furnace while being caused to flow.

The molding step is a step of molding the obtained calcinated product.

A method of molding the calcinated product is not particularly limited, and the calcinated product can be molded into any shape using a molding machine for an ordinary powder such as a tablet molding machine, an extrusion molding machine, and a tumbling granulator.

At the time of molding the calcinated product, a conventionally known additive, for example, an organic compound such as polyvinyl alcohol or carboxymethyl cellulose may be further added. Furthermore, an inorganic compound such as graphite and diatomaceous earth and an inorganic fiber such as a glass fiber, a ceramic fiber, and a carbon fiber may be added.

The obtained molded product may be supported on a carrier. As the carrier that is used at the time of supporting the molded product, silica, alumina, silica-alumina, magnesia, titania, silicon carbide, and the like are exemplary examples. In addition, the catalyst can also be used after being diluted with an inert substance such as silica, alumina, silica-alumina, magnesia, titania, or silicon carbide.

[Use of Catalyst]

While not particularly limited, the catalyst according to the present embodiment can be suitably used as a catalyst for producing unsaturated aldehydes and/or unsaturated carboxylic acids. For example, unsaturated aldehydes and/or unsaturated carboxylic acids can be produced with a high selectivity by performing a gas phase oxidation reaction of an organic compound in the presence of the catalyst. Specifically, corresponding unsaturated aldehydes and/or unsaturated carboxylic acids can be produced with a high selectivity by performing a gas phase oxidation reaction of propylene, isobutylene, t-butyl alcohol, methyl-t-butyl ether, or the like (hereinafter, also referred to as the raw material organic compound) in the presence of the catalyst.

For example, an unsaturated aldehyde corresponding to propylene is acrolein, and an unsaturated carboxylic acid corresponding to propylene is acrylic acid. In addition, an unsaturated aldehyde corresponding to isobutylene is methacrolein, and an unsaturated carboxylic acid corresponding to isobutylene is methacrylic acid. An unsaturated aldehyde corresponding to t-butyl alcohol is methacrolein, and an unsaturated carboxylic acid corresponding to t-butyl alcohol is methacrylic acid. An unsaturated aldehyde corresponding to methyl-t-butyl ether is methacrolein, and an unsaturated carboxylic acid corresponding to methyl-t-butyl ether is methacrylic acid.

Specifically, unsaturated aldehydes and/or unsaturated carboxylic acids can be produced by, for example, bringing the catalyst and a raw material gas containing the raw material organic compound and molecular oxygen into contact with in a reactor.

The reactor is not particularly limited, a reactor that is ordinarily used for gas phase oxidation can be used, in particular, a tubular reactor including a reaction tube packed with a catalyst is preferably used, and, industrially, a multi-tube reactor including a plurality of reaction tubes is particularly preferably used.

The concentration of the raw material organic compound in the raw material gas is not particularly limited, but is preferably 1% by volume or more and 20% by volume or less and, particularly, more preferably 3% by volume or more and, on the other hand, is more preferably 10% by volume or less.

A molecular oxygen source for the raw material gas is not particularly limited, but the use of an air is industrially advantageous. In addition, if necessary, a gas obtained by mixing pure oxygen with an air or the like can also be used.

The proportion of the molecular oxygen with respect to the raw material organic compound in the raw material gas is not particularly limited, but is preferably 10% by volume or more and 500% by volume or less and, particularly, more preferably 50% by volume or more and, on the other hand, is more preferably 300% by volume or less. From an economical viewpoint, the raw material gas is preferably used after being diluted with an inert gas such as nitrogen or carbon dioxide, water vapor, or the like.

The reaction pressure during the gas phase oxidation reaction is not particularly limited, but is usually approximately several atmospheric pressures from the atmospheric pressure.

The reaction temperature is not particularly limited, but is preferably 200° C. or higher and more preferably 250° C. or higher and, on the other hand, is preferably 450° C. or lower and more preferably 400° C. or lower.

The contact time between the raw material gas and the catalyst is not particularly limited, but is preferably 0.5 seconds or longer and more preferably 1.0 second or longer and, on the other hand, is preferably 10 seconds or shorter and more preferably 5.0 seconds or shorter.

Due to such gas-phase oxidation, an unsaturated aldehyde and an unsaturated carboxylic acid corresponding to the raw material organic compounds used can be obtained with a high selectivity. For example, when propylene is used as the raw material organic compound, acrolein and/or acrylic acid can be obtained with a high selectivity. When isobutylene is used as the raw material organic compound, methacrolein and/or methacrylic acid can be obtained with a high selectivity. When TBA is used as the raw material organic compound, methacrolein and/or methacrylic acid can be obtained with a high selectivity. When MTBE is used as the raw material organic compound, methacrolein and/or methacrylic acid can be obtained with a high selectivity.

EXAMPLES

Hereinafter, production examples of the catalyst according to the present invention and reaction examples in which the catalysts were used will be described together with comparative examples. "Parts" in the following examples and comparative examples is "parts by mass". Analysis in reaction evaluation was carried out by gas chromatography.

Activity tests of catalysts in the examples and the comparative examples were carried out using the gas phase oxidation of isobutylene with molecular oxygen as an example. The reaction rates of raw materials and the selectivity of methacrolein (MAL) and methacrylic acid (MAA) that are generated are each defined as described below.

Total selectivity (%) of MAL and MAA=((number of moles of MAL generated+number of moles of MAA generated)/number of moles of isobutylene reacted)×100

Example 1

(Catalyst Preparation)

500 Parts by mass of ammonium paramolybdate tetrahydrate, 12.3 parts by mass of ammonium paratungstate, 27.6 parts by mass of cesium nitrate, 38.5 parts by mass of bismuth oxide, and 20.6 parts by mass of antimony trioxide having an average particle size of 1.0 μm as an antimony raw material were mixed with 2,000 parts by mass of pure water (60° C.), and then 3.5 parts by mass of hydrazine monohydrate (0.30 mol with respect to 12 mol of molybdenum atoms of ammonium paramolybdate) as a dispersant) was added thereto and mixed therewith, thereby prepare a first liquid. In addition, separately from the first liquid, 200.2 parts by mass of iron (III) nitrate nonahydrate and 515.1 parts by mass of cobalt (II) nitrate hexahydrate were sequentially added to and dissolved in 1,000 parts by mass of pure water, thereby preparing a second liquid.

Next, the second liquid was added to the first liquid to obtain a slurry (raw material liquid). This slurry was heated up to 95° C. and aged for 1 hour. After that, the slurry was dried with a spray dryer. The slurry was dried under conditions of an inlet hot air temperature of 250° C., an outlet temperature of 120° C. to 130° C., and a rotary atomizer rotation speed of 15,000 rpm. The obtained dry powder did not adhere to the inner wall surface of the spray dryer and was in a favorable dry state. Furthermore, the dry powder was thermally treated at 300° C. for 1 hour in an air atmosphere and then pulverized. Subsequently, the pulverized dry powder was pressure-molded, and the pressure-molded product was pulverized to obtain pulverized particles. After that, the pulverized particles were classified and passed through a sieve having a mesh size of 2.36 mm, and pulverized particles that failed to pass through a sieve having a mesh size of 0.71 mm were collected. After that, the collected pulverized particles were thermally treated again at 500° C. for 6 hours in an air atmosphere to obtain a catalyst. The composition of the elements of the catalyst thus obtained (excluding oxygen) was $Mo_{12}Bi_{0.70}Fe_{2.10}Co_{7.50}W_{0.20}Sb_{0.60}Cs_{0.60}$.

(Reaction Evaluation)

The obtained catalyst was packed into a stainless steel reaction tube to form a catalyst layer, then, a raw material gas having a composition of 5% by volume of isobutylene (raw material), 12% by volume of oxygen, 10% by volume of water vapor, and 73% by volume of nitrogen was passed through the catalyst layer in the reaction tube with a contact time of 2.7 seconds and reacted at 340° C., and the reaction of the catalyst was evaluated. The results are shown in Table 1.

Example 2

A catalyst was produced by the same method as in Example 1 except that the amount of antimony trioxide used was changed from 20.6 parts to 24.7 parts by mass, and the amount of hydrazine monohydrate used was changed from used, and the reaction of the catalyst was evaluated. The obtained results are shown in Table 1.

TABLE 1

| | Number of antimony atoms/number of molybdenum atoms in entire catalyst | Number of antimony atoms/number of molybdenum atoms on a surface of catalyst | Surface/entire | MAL + MAA selectivity [%] |
|---|---|---|---|---|
| Example 1 | 0.084 | 0.206 | 2.453 | 91.2 |
| Example 2 | 0.101 | 0.269 | 2.669 | 91.3 |
| Example 3 | 0.084 | 0.249 | 2.958 | 91.5 |
| Example 4 | 0.084 | 0.145 | 1.726 | 91.2 |
| Example 5 | 0.105 | 0.209 | 1.991 | 90.7 |
| Comparative Example 1 | 0.084 | 0.065 | 0.773 | 89.8 |
| Comparative Example 2 | 0.084 | 0.080 | 0.952 | 90.0 |

3.5 parts by mass to 1.2 parts by mass (0.10 mol with respect to 12 mol of molybdenum atoms in ammonium paramolybdate), and the reaction of the catalyst was evaluated. The composition of the elements of the catalyst thus obtained (excluding oxygen) was $Mo_{12}Bi_{0.70}Fe_{2.10}Co_{7.50}W_{0.20}Sb_{0.72}Cs_{0.60}$. The obtained results are shown in Table 1.

Example 3

A catalyst was produced by the same method as in Example 1 except that the amount of hydrazine monohydrate used was changed from 3.5 parts by mass to 2.3 parts by mass (0.20 mol with respect to 12 mol of molybdenum atoms in ammonium paramolybdate), and the reaction of the catalyst was evaluated. The obtained results are shown in Table 1.

Example 4

A catalyst was produced by the same method as in Example 1 except that the amount of hydrazine monohydrate used was changed from 3.5 parts by mass to 0.81 parts by mass (0.07 mol with respect to 12 mol of molybdenum atoms in ammonium paramolybdate), and the reaction of the catalyst was evaluated. The obtained results are shown in Table 1.

Example 5

A catalyst was produced by the same method as in Example 1 except that the amount of antimony trioxide used was changed from 20.6 parts to 26.8 parts by mass, and the reaction of the catalyst was evaluated. The obtained results are shown in Table 1.

Comparative Example 1

A catalyst was produced by the same method as in Example 1 except that the average particle size of antimony trioxide was changed to 0.20 μm, and the reaction of the catalyst was evaluated. The obtained results are shown in Table 1.

Comparative Example 2

A catalyst was produced by the same method as in Comparative Example 1 except that the dispersant was not From the results in Table 1, it is found that, in Examples 1 to 5 wherein the atom ratio of the antimony to the molybdenum on the surface of the catalyst was greater than the atom ratio of the antimony to the molybdenum in the entire catalyst, the total selectivity was 90.7 to 91.5%, and methacrolein and methacrylic acid were obtained with a high selectivity.

What is claimed is:

1. A catalyst comprising molybdenum, antimony, bismuth and iron, wherein an atom ratio of the antimony to the molybdenum on a surface of the catalyst is greater than an atom ratio of the antimony to the molybdenum in an entire catalyst, a ratio B/A is 1.2 to 10.0, in which A is an atom ratio of the antimony to the molybdenum calculated by Inductively Coupled Plasma (ICP) emission spectroscopy, and B is a peak area ratio of the antimony to the molybdenum calculated by X-ray photoelectron spectroscopy, and the catalyst comprises Formula (1):

$$Mo_aBi_bFe_cSb_dM_eX_fY_gSi_hO_i \qquad (1)$$

wherein, in Formula (1),

Mo, Bi, Fe, Sb, Si and O represent molybdenum, bismuth, iron, antimony, silicon and oxygen, respectively, M represents at least one selected from the group consisting of cobalt and nickel, X represents at least one element selected from the group consisting of zinc, chromium, lead, manganese, calcium, magnesium, niobium, silver, barium, tin, thallium, tungsten, phosphorus, boron, sulfur, selenium, tellurium, cerium and titanium, Y represents at least one element selected from the group consisting of cesium, lithium, sodium, potassium, rubidium and thallium, a, b, c, d, e, f, g, h and i represent an atomic ratio, a=12, b=0.01 to 3.00, c=0.01 to 5.00, d=0.01 to 5.00, e=0.00 to 12.00, f=0.00 to 8.00, g=0.001 to 2.00, h=0.00 to 20.00, and i represents an oxygen atom ratio required to satisfy a valence of each component.

2. The catalyst according to claim 1, wherein A is 0.04 or more and 0.20 or less.

3. The catalyst according to claim 1, wherein B is 0.05 or more and 0.50 or less.

4. A method of producing an unsaturated aldehyde and/or an unsaturated carboxylic acid, comprising:

performing a gas phase oxidation reaction of an organic compound as a raw material in presence of the catalyst according to claim 1, wherein the organic compound comprises at least one selected from the group consisting of propylene, isobutylene, t-butyl alcohol, and methyl-t-butyl ether.

5. A method of producing a catalyst containing molybdenum and antimony, comprising:

mixing a molybdenum compound, an antimony compound, and a dispersant to produce a mixture; and calcinating the mixture to produce the catalyst;

wherein, in the mixing, the dispersant is added before the antimony compound is dissolved, an atom ratio of the antimony to the molybdenum on a surface of the catalyst is greater than an atom ratio of the antimony to the molybdenum in an entire catalyst a ratio B/A is 1.2 to 10.0, in which A is an atom ratio of the antimony to the molybdenum calculated by Inductively Coupled Plasma (ICP) emission spectroscopy, and B is a peak area ratio of the antimony to the molybdenum calculated by X-ray photoelectron spectroscopy, and the catalyst comprises Formula (1):

$$Mo_aBi_bFe_cSb_dM_eX_fY_gSi_hO_i \qquad (1)$$

wherein, in Formula (1),

Mo, Bi, Fe, Sb, Si and O represent molybdenum, bismuth, iron, antimony, silicon and oxygen, respectively, M represents at least one selected from the group consisting of cobalt and nickel, X represents at least one element selected from the group consisting of zinc, chromium, lead, manganese, calcium, magnesium, niobium, silver, barium, tin, thallium, tungsten, phosphorus, boron, sulfur, selenium, tellurium, cerium and titanium, Y represents at least one element selected from the group consisting of cesium, lithium, sodium, potassium, rubidium and thallium, a, b, c, d, e, f, g, h and i represent an atomic ratio, a=12, b=0.01 to 3.00, c=0.01 to 5.00, d=0.01 to 5.00, e=0.00 to 12.00, f=0.00 to 8.00, g=0.001 to 2.00, h=0.00 to 20.00, and i represents an oxygen atom ratio required to satisfy a valence of each component.

6. The method according to claim 5, wherein the dispersant comprises a hydrazine compound.

7. The method according to claim 5, wherein the antimony compound has a particle size of 0.21 μm or more and 7.90 μm or less.

8. The catalyst according to claim 1, wherein the ratio B/A is 1.2 or more and 8.0 or less.

9. The catalyst according to claim 1, wherein the ratio B/A is 1.5 or more and 6.0 or less.

10. The catalyst according to claim 1, wherein the ratio B/A is 1.8 or more and 4.0 or less.

11. The catalyst according to claim 1, wherein the ratio B/A is 2.0 or more and 3.5 or less.

12. The catalyst according to claim 1, wherein A is 0.06 or more and 0.16 or less.

13. The catalyst according to claim 1, wherein A is 0.08 or more and 0.12 or less.

14. The catalyst according to claim 1, wherein B is 0.13 or more and 0.40 or less.

15. The catalyst according to claim 1, wherein B is 0.15 or more and 0.35 or less.

* * * * *